(12) United States Patent
Ueya

(10) Patent No.: US 9,958,445 B2
(45) Date of Patent: *May 1, 2018

(54) SOLID-PHASE SUPPORT, LIGAND-BINDING SOLID-PHASE SUPPORT, METHOD FOR DETECTING OR SEPARATING TARGET SUBSTANCE, AND METHOD FOR PRODUCING THE SOLID-PHASE SUPPORT

(71) Applicants: JSR CORPORATION, Minato-ku (JP); JSR Life Sciences Corporation, Minato-ku (JP)

(72) Inventor: Yuuichi Ueya, Minato-ku (JP)

(73) Assignees: JSR CORPORATION, Minato-ku (JP); JSR LIFE SCIENCES CORPORATION, Minato-ku (JP)

(*) Notice: Subject to any disclaimer, the term of this patent is extended or adjusted under 35 U.S.C. 154(b) by 0 days. days.

This patent is subject to a terminal disclaimer.

(21) Appl. No.: 14/847,539

(22) Filed: Sep. 8, 2015

(65) Prior Publication Data

US 2016/0069870 A1    Mar. 10, 2016

(30) Foreign Application Priority Data

Sep. 8, 2014  (JP) .................... 2014-182070

(51) Int. Cl.
G01N 33/545 (2006.01)
C07K 1/14 (2006.01)
C07K 1/16 (2006.01)
G01N 33/543 (2006.01)

(52) U.S. Cl.
CPC ............. *G01N 33/545* (2013.01); *C07K 1/16* (2013.01); *G01N 33/54326* (2013.01); *G01N 2446/20* (2013.01)

(58) Field of Classification Search
CPC .... C07F 9/587; C07F 9/65036; C07F 9/6539; C07F 9/655345; C07K 16/44; C07K 14/001; G01N 33/5308; G01N 2440/14
See application file for complete search history.

(56) References Cited

U.S. PATENT DOCUMENTS

2008/0139399 A1*  6/2008  Fonnum ................ C08F 287/00
                                                                506/9
2009/0061533 A1   3/2009  Minami et al.

FOREIGN PATENT DOCUMENTS

JP       2009-069141        4/2009
JP       2009-542862        12/2009
WO    WO 2008003099 A1 *  1/2008 ............ C08F 287/00

* cited by examiner

*Primary Examiner* — Shafiqul Haq
(74) *Attorney, Agent, or Firm* — Oblon, McClelland, Maier & Neustadt, L.L.P.

(57) ABSTRACT

A solid-phase support, formed by binding a chain polymer at least to the surface, wherein the chain polymer is a block polymer comprising a first block constituted from repetitions of a hydrophilic structural unit and a second block constituted from repetitions of a structural unit having a reactive functional group, a content ratio of the number of moles "a" of the reactive functional group contained in the chain polymer and the number of moles "b" of the whole structural unit contained in the chain polymer, (a/b), is from 0.03 to 0.25, and a density of the chain polymer occupying the surface of the solid-phase support is 0.1 polymers/nm$^2$ or more.

13 Claims, No Drawings

SOLID-PHASE SUPPORT, LIGAND-BINDING SOLID-PHASE SUPPORT, METHOD FOR DETECTING OR SEPARATING TARGET SUBSTANCE, AND METHOD FOR PRODUCING THE SOLID-PHASE SUPPORT

FIELD OF THE INVENTION

The present invention relates to a solid-phase support, a ligand-binding solid-phase support, a method for detecting or separating a target substance, and a method for producing the solid-phase support.

BACKGROUND OF THE INVENTION

A solid-phase support is used for the purpose of detecting and separating a target substance such as a protein, a nucleic acid and a cell from sample such as blood. As the method of detection and separation using a solid-phase support, a general method is that a ligand is fixed to a solid-phase support, with which a sample is brought into contact to allow a target substance to react with the ligand. At the time of the above contact, however, the target substance and impurities in the sample nonspecifically adsorb on a surface of the solid-phase support instead of the ligand, which may cause noise.

Therefore, for the purpose of suppressing the above nonspecific adsorption, a technique is suggested, in which an atom transfer radical polymerization initiating group (ATRP initiating group) is introduced on the surface of the gold film chip in a magnetic biosensor in a content amount and a specific carboxybetaine monomer is polymerized from such ATRP initiating group to form a polymer brush (JP 2009-69141 A).

A ligand is, however, hard to bind to the above gold film chip having a polymer brush, which may not sufficiently grasp a target substance.

In the meantime, an interest has focused on a magnetic bead as a solid-phase support used for a diagnostic agent for enzyme immunoassay in a clinical examination in recent years. Early detection of diseases, for example, is required, and thus it is demanded that the magnetic bead used for the diagnostic agent is sufficiently grasp a target substance.

SUMMARY OF THE INVENTION

In contrast, a magnetic bead is suggested in which a poly(hydroxyethyl methacrylamide)-poly(methacrylic acid) block copolymer, for example, is allowed to bind to the surface by ATRP to form a polymer brush (JP 2009-542862 W).

In the magnetic bead described in JP 2009-542862 W, however, a target substance and impurities in a sample are easy to nonspecifically adsorb on the bead surface, and there has been room for improvement in this respect.

Therefore, an object of the present invention is to provide a solid-phase support, to which a ligand easily binds, and in which nonspecific adsorption is suppressed.

Under the above circumstances, the present inventors analyzed and investigated various physical properties of the magnetic beads described in JP 2009-542862 W, and found that a high amount of reactive functional group is contained in the block copolymer (content ratio=about 0.27).

As a result of further investigation, the present inventors found that when, in a solid-phase support formed by binding a block copolymer comprising a first block constituted from repetitions of a hydrophilic structural unit and a second block constituted from repetitions of a structural unit having a reactive functional group at least to the surface, a content ratio of the number of moles "a" of the reactive functional group and the number of moles "b" of the whole structural unit, (a/b), is from 0.03 to 0.25 and a density occupied by the chain polymer is 0.1 polymers/nm$^2$ or more, a solid-phase support, to which a ligand easily binds, and in which nonspecific adsorption is suppressed, is obtained, thereby completing the present invention.

That is, the present invention provides <1> a solid-phase support, formed by binding a chain polymer at least to the surface, wherein the chain polymer is a block polymer comprising a first block constituted from repetitions of a hydrophilic structural unit and a second block constituted from repetitions of a structural unit having a reactive functional group, a content ratio of the number of moles "a" of the reactive functional group contained in the chain polymer and the number of moles "b" of the entire structural unit contained in the chain polymer, (a/b), is from 0.03 to 0.25, and a density of the chain polymer occupying the surface of the solid-phase support is 0.1 polymers/nm$^2$ or more.

The present invention also provides <2> a ligand-binding solid-phase support, formed by binding a ligand to the solid-phase support according to <1> above.

The present invention further provides <3> a method for detecting or separating a target substance in a sample, the method using the ligand-binding solid-phase support according to <2> above.

The present invention further provides <4> a method for producing the solid-phase support according to <1> above, the method comprising: (Step 1) a step of preparing a support having a polymerization initiating group at least on the surface, and (Step 2) a step of polymerizing a monomer from the polymerization initiating group.

EFFECT OF THE INVENTION

The solid-phase support of the present invention is a solid-phase support, to which a ligand easily binds, and in which a target substance and impurities in a sample are hard to adsorb on the surface and nonspecific adsorption is suppressed.

According to the production method of the present invention, a solid-phase support to which a ligand easily binds, and in which a target substance and impurities in a sample are hard to adsorb on the surface and nonspecific adsorption is suppressed can be simply produced.

DETAILED DESCRIPTION OF THE INVENTION

<Solid-Phase Support>

The solid-phase support of the present invention is a solid-phase support formed by binding a chain polymer at least to the surface, in which the above chain polymer is a block polymer comprising a first block constituted from repetitions of a hydrophilic structural unit and asecond block constituted from repetitions of a structural unit having a reactive functional group, a content ratio of the number of moles "a" of the reactive functional group contained in the above chain polymer and the number of moles "b" of the whole structural unit contained in the above chain polymer, (a/b), is from 0.03 to 0.25, and a density of the above chain polymer occupying the surface of the above solid-phase support is 0.1 polymers/nm$^2$ or more. At the outset, the solid-phase support of the present invention is described in detail.

(First Block)

The first block is constituted from repetitions of a hydrophilic structural unit.

As the hydrophilic structural unit, a structural unit having a hydrophilic group is preferred and a structural unit having a hydrophilic group on a side chain is more preferred. The number of hydrophilic groups is preferably 1 to 3 and more preferably 1 per the above structural unit.

Examples of the structural unit having a hydrophilic group on a side chain include a structural unit derived from a (meth)acrylate monomer having a hydrophilic group, a structural unit derived from a (meth) acrylamide monomer having a hydrophilic group, and a structural unit derived from a styrene monomer having a hydrophilic group. Among these, a structural unit derived from a (meth)acrylate monomer having a hydrophilic group and a structural unit derived from a (meth)acrylamide monomer having a hydrophilic group are preferred in terms of the suppression of nonspecific adsorption.

In the present description, hydrophilicity means to have a strong affinity for water. Specifically, when a homopolymer comprising only one structural unit (the number average molecular weight by a method of measurement in Example is about from 1,000 to 100,000) is dissolved in an amount of 1 g or more in 100 g of pure water at normal temperature (25° C.), the structural unit is hydrophilic.

Examples of the hydrophilic group include a hydroxy group, an alkoxy group, a polyoxyalkylene group, a group having a zwitterionic structure, a sulfonyl group, a sulfinyl group and a phosphate group, and a structural unit may have one of these groups or may have two or more of these groups. As the alkoxy group, an alkoxy group having one or two carbons is preferred. Examples thereof include, for example, a methoxy group and an ethoxy group.

Among these groups, as the hydrophilic group, a hydroxy group, a group having a zwitterionic structure, a polyoxyalkylene group and a phosphate group are preferred, and a hydroxy group, a group having a zwitterionic structure and a polyoxyalkylene group are more preferred in terms of suppressing nonspecific adsorption.

As the above polyoxyalkylene group, a group represented by —$(R^aO)_q$— ($R^a$ represents an alkanediyl group and q represents an integer from 2 to 100, and q groups of $R^a$s may be the same or different) is preferred.

The number of carbons in an alkanediyl group represented by $R^a$ is preferably from 2 to 4, more preferably 2 or 3 and especially preferably 2.

In addition, the alkanediyl group represented by $R^a$ may be a straight chain or a branched chain, and specific examples thereof include, for example, an ethane-1,2-diyl group, a propane-1,2-diyl group, a propane-1,3-diyl group and a propane-2,2-diyl group. Among these groups, an ethane-1,2-diyl group is preferred.

q represents an integer from 2 to 100, and an integer from 3 to 80 is preferred, an integer from 4 to 60 is more preferred, an integer from 5 to 40 is further preferred, an integer from 6 to 30 is further preferred, and an integer from 7 to 20 is especially preferred.

As the above group having a zwitterionic structure, an organic group having a quaternary ammonium salt cationic functional group and a monovalent or divalent anionic functional group selected from the group consisting of —(C=O)O⁻, —$SO_3^-$ and —O—(O=P—O⁻)—O— is preferred, an organic group represented by the following formula (1) or (2) is more preferred, and an organic group represented by the following formula (1) is especially preferred in terms of suppressing nonspecific adsorption.

[In the formula (1),
$R^1$ and $R^2$ each independently represent a single bond or a divalent organic group having 1 to 10 carbons,
$R^3$ represents —(C=O)O⁻ or —$SO_3^-$, and
$R^4$ and $R^5$ each independently represent a methyl group or an ethyl group.]

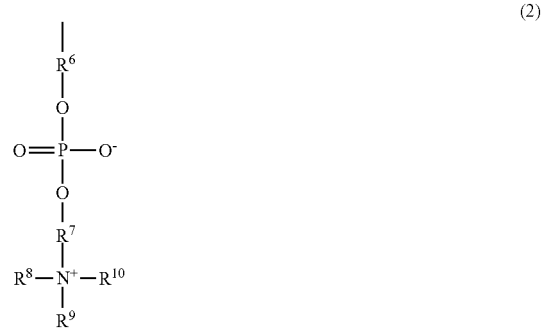

[In the formula (2),
$R^6$ and $R^7$ each independently represent a single bond or a divalent organic group having 1 to 10 carbons, and
$R^8$, $R^9$ and $R^{10}$ each independently represent a methyl group or an ethyl group.]

$R^1$ and $R^2$ in the formula (1) and $R^6$ and $R^7$ in the formula (2) each independently represent a single bond or a divalent organic group having from 1 to 10 carbons, and in terms of suppressing nonspecific adsorption, a divalent organic group having from 1 to 10 carbons is preferred, a divalent hydrocarbon group having from 1 to 10 carbons and a group having one or more selected from the group consisting of an ether bond, an amide bond and an ester bond between carbon and carbon atoms in a divalent hydrocarbon group having from 2 to 10 carbons is more preferred, and a divalent hydrocarbon group having from 1 to 10 carbons is especially preferred.

When the divalent organic group is a divalent hydrocarbon group, the number of carbons is preferably from 1 to 8, more preferably from 1 to 6, further preferably from 1 to 4, and especially preferably from 1 to 3. Meanwhile, when the divalent organic group is a group having one or more selected from the group consisting of an ether bond, an amide bond and an ester bond between carbon and carbon atoms in a divalent hydrocarbon group, the number of carbons of the divalent hydrocarbon group in such a group is preferably from 2 to 8, more preferably from 2 to 6, further preferably from 2 to 4, and especially preferably 2 or 3.

As the "divalent hydrocarbon group" in $R^1$, $R^2$, $R^6$ and $R^7$, a divalent aliphatic hydrocarbon group is preferred. Such a divalent aliphatic hydrocarbon group may be a straight chain or a branched chain.

As the above divalent aliphatic hydrocarbon group, an alkanediyl group is preferred and specific examples thereof include, for example, a methane-1,1-diyl group, an ethane-1,1-diyl group, an ethane-1,2-diyl group, a propane-1,1-diyl group, a propane-1,2-diyl group, a propane-1,3-diyl group, a propane-2,2-diyl group, a butane-1,2-diyl group, a butane-1,3-diyl group, a butane-1,4-diyl group, a pentane-1,4-diyl group, a pentane-1,5-diyl group, a hexane-1,5-diyl group and a hexane-1,6-diyl group.

$R^3$ in the formula (1) is preferably —(C=O)O$^-$.

$R^4$ and $R^5$ in the formula (1) and $R^8$, $R^9$ and $R^{10}$ in the formula (2) are preferably a methyl group.

In addition, suitable specific examples of the hydrophilic structural unit include a structural unit represented by the following formula (3).

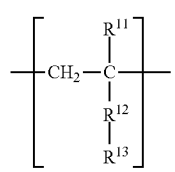

[In the formula (3), $R^{11}$ represents a hydrogen atom or a methyl group, $R^{12}$ represents —(C=O)—O—*, —(C=O)—NR$^{14}$—*, where $R^{14}$ represents a hydrogen atom or a methyl group, and * represents a position bound to $R^{13}$ in the formula (3), or a phenylene group, and $R^{13}$ represents a group having a zwitterionic structure, an organic group having a hydroxy group, or an organic group having a polyoxyalkylene group.]

In the formula (3), $R^{12}$ is preferably —(C=O)—O—* or —(C=O)—NH—* in terms of suppressing nonspecific adsorption.

The group having a zwitterionic structure represented by $R^{13}$ is the same as the above groups having a zwitterionic structure.

Examples of the organic group having a hydroxy group represented by $R^{13}$ include a group represented by the following formula (4).

[In the formula (4), $R^{15}$ represents a divalent organic group.]

Examples of the divalent organic group represented by $R^{15}$ include a divalent hydrocarbon group and a group having one or more selected from the group consisting of an ether bond, an amide bond and an ester bond between carbon and carbon atoms in a divalent hydrocarbon group having 2 or more carbons, and a divalent hydrocarbon group is preferred.

When the divalent organic group is a divalent hydrocarbon group, the number of carbons is preferably from 1 to 8, more preferably from 1 to 6, further preferably from 1 to 4, and especially preferably from 1 to 3. Meanwhile, when the divalent organic group is a group having one or more selected from the group consisting of an ether bond, an amide bond and an ester bond between carbon and carbon atoms in a divalent hydrocarbon group having 2 or more carbons, the number of carbons of the divalent hydrocarbon group in such a group is preferably from 2 to 8, more preferably from 2 to 6, further preferably from 2 to 4, and especially preferably 2 or 3.

As the "divalent hydrocarbon group" in $R^{15}$, a divalent aliphatic hydrocarbon group is preferred. Such a divalent aliphatic hydrocarbon group may be a straight chain or a branched chain.

As the above divalent aliphatic hydrocarbon group, an alkanediyl group is preferred and specific examples thereof include, for example, a methane-1,1-diyl group, an ethane-1,1-diyl group, an ethane-1,2-diyl group, a propane-1,1-diyl group, a propane-1,2-diyl group, a propane-1,3-diyl group, a propane-2,2-diyl group, a butane-1,2-diyl group, a butane-1,3-diyl group, a butane-1,4-diyl group, a pentane-1,4-diyl group, a pentane-1,5-diyl group, a hexane-1,5-diyl group, and a hexane-1,6-diyl group.

As the organic group having a polyoxyalkylene group represented by $R^{13}$, a group represented by —(R$^a$O)$_q$—R$^b$ is preferred, where $R^b$ represents an alkyl group having 1 to 4 carbons. $R^a$ and q have the same meaning as above, $R^a$ represents an alkanediyl group and q represents an integer from 2 to 100, respectively.

The number of carbons in an alkyl group represented by $R^b$ is preferably 1 to 3 and more preferably 1 or 2. In addition, the alkyl group represented by $R^b$ may be a straight chain or a branched chain, and specific examples thereof include a methyl group, an ethyl group, a n-propyl group, an isopropyl group, a n-butyl group, an isobutyl group, a sec-butyl group and a tert-butyl group, and a methyl group is especially preferred.

(Second Block)

The second block is constituted from repetitions of a structural unit having a reactive functional group. As the structural unit having a reactive functional group, a structural unit having a reactive functional group on a side chain is preferred. The number of reactive functional groups is preferably 1 to 3 and more preferably 1 per the above structural unit.

Examples of the structural unit having a reactive functional group on a side chain include a structural unit derived from (meth)acrylic acid or salts thereof, a structural unit derived from a (meth)acrylate monomer having a reactive functional group, a structural unit derived from a (meth)acrylamide monomer having a reactive functional group, and a structural unit derived from a styrene monomer having a reactive functional group. Among these, a structural unit derived from (meth)acrylic acid or salts thereof, a structural unit derived from a (meth)acrylate monomer having a reactive functional group and a structural unit derived from a (meth)acrylamide monomer having a reactive functional group are preferred in terms of suppressing nonspecific adsorption.

Examples of the reactive functional group include a carboxy group, a tosyl group, an amino group, an epoxy group, an acyl group and an azide group, and a structural unit may have one or two or more of these groups. Among these groups, a carboxy group, a tosyl group, an amino group and an epoxy group are preferred in terms of preventing a bound ligand from coming off and from the point that, when a biomolecule such as a protein or a nucleic acid is used as a ligand, the biomolecule can bind to a solid-phase support using a functional group which the ligand originally has, and a carboxy group is more preferred, for example, from the point that a ligand is easily allowed to simply and quickly bind to a solid-phase support.

A content of the reactive functional group per g of solid content in a solid-phase support is preferably 1 µmol or more, more preferably 5 µmol or more, further preferably 10 µmol or more, further preferably 15 µmol or more, further preferably 20 µmol or more and especially preferably 30 µmol or more in terms of the amount of bound ligand and in terms of achieving both an increase in sensitivity and a decrease in noise in detection, and is also preferably 300 µmol or less, more preferably 200 µmol or less, further preferably 175 μmol or less, and especially preferably 150 μmol or less in terms of suppressing nonspecific adsorption.

The content of the reactive functional group can be, for example when the reactive functional group is a carboxy group, measured by, for example, conductometry, and specifically can be measured in accordance with a method described in the examples mentioned below. In addition, when the reactive functional group is a tosyl group, the content can be obtained by, for example, measuring an absorption of the ultraviolet-visible light of a tosyl group introduced into a solid-phase support, and when the reactive functional group is an amino group, the content can be obtained by, for example, allowing an amino group to react with N-succinimidyl-3-(2-pyridyldithio)propionate, followed by reduction, and measuring the absorbance of free thiopyridyl group.

Suitable specific examples of the structural unit having a reactive functional group on a side chain include a structural unit represented by the following formula (5).

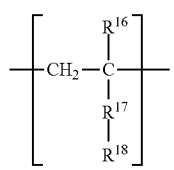
(5)

[In the formula (5), $R^{16}$ represents a hydrogen atom or a methyl group, $R^{17}$ represents —(C=O)—O—*, —(C=O)—NR$^{19}$—* ($R^{19}$ represents a hydrogen atom or a methyl group, and * represents a position bound to $R^{18}$ in the formula (5)) or a phenylene group, and when $R^{17}$ is —(C=O)—O—*, $R^{18}$ represents a hydrogen atom or an organic group having a reactive functional group, and when $R^{17}$ is —(C=O)—NR$^{19}$—* or a phenylene group, $R^{18}$ represents an organic group having a reactive functional group.]

In the formula (5), $R^{17}$ is preferably —(C=O)—O—* or —(C=O)—NR$^{19}$—* in terms of increasing affinity for water and suppressing nonspecific adsorption. $R^{19}$ represents a hydrogen atom or a methyl group, and a hydrogen atom is preferred.

As the organic group having a reactive functional group represented by $R^{18}$, an organic group represented by the following formula (6) is preferred. The reactive functional group in $R^{18}$ is the same as above.

[In the formula (6), $R^{20}$ represents a divalent organic group, and

Y represents a reactive functional group.]

Examples of the divalent organic group represented by $R^{20}$ include a divalent hydrocarbon group and a group having one or more selected from the group consisting of an ether bond, an imino group, an amide bond and an ester bond between carbon and carbon atoms in a divalent hydrocarbon group having 2 or more carbons.

When the divalent organic group is a divalent hydrocarbon group, the number of carbons is preferably from 1 to 10, more preferably from 1 to 8, and especially preferably from 1 to 6. Meanwhile, when the divalent organic group is a group having one or more selected from the group consisting of an ether bond, an imino group, an amide bond and an ester bond between carbon and carbon atoms in a divalent hydrocarbon group having two or more carbons, the number of carbons of the divalent hydrocarbon group in such a group is preferably from 2 to 10, more preferably from 2 to 8, and especially preferably from 2 to 6.

As the "divalent hydrocarbon group" in $R^{20}$, a divalent aliphatic hydrocarbon group is preferred. Such a divalent aliphatic hydrocarbon group may be a straight chain or a branched chain.

As the above divalent aliphatic hydrocarbon group, an alkanediyl group is preferred and specific examples thereof include, for example, a methane-1,1-diyl group, an ethane-1,1-diyl group, an ethane-1,2-diyl group, a propane-1,1-diyl group, a propane-1,2-diyl group, a propane-1,3-diyl group, a propane-2,2-diyl group, a butane-1,2-diyl group, a butane-1,3-diyl group, a butane-1,4-diyl group, a pentane-1,4-diyl group, a pentane-1,5-diyl group, a hexane-1,5-diyl group, a hexane-1,6-diyl group.

As the group having one or more selected from the group consisting of an ether bond, an imino group, an amide bond and an ester bond between carbon and carbon atoms in a divalent hydrocarbon group having two or more carbons, a group having an ester bond between carbon and carbon atoms in the divalent hydrocarbon group having 2 or more carbons is preferred, and a divalent group represented by —R$^c$—O(C=O)—R$^d$—*, where R$^c$ and R$^d$ each independently represent an alkanediyl group having 2 to 4 carbons, and * represents a position bound to Y in the formula (6), is more preferred, for example, in terms of obtaining a chain polymer in a simple manner. The number of carbons in an alkanediyl group is preferably 2 or 3 and more preferably 2. The alkanediyl group may be a straight chain or a branched chain, and examples thereof include an ethane-1,2-diyl group, a propane-1,2-diyl group and a propane-1,3-diyl group.

As the above combination of $R^{17}$ and $R^{18}$, a combination of —(C=O)—O—* as $R^{17}$ and a hydrogen atom or an organic group having a reactive functional group as $R^{18}$, and a combination of —(C=O)—NR$^{19}$—* as $R^{17}$ and an organic group having a reactive functional group as $R^{18}$ are preferred, and a combination of —(C=O)—O—* as $R^{17}$ and a hydrogen atom as $R^{18}$, and a combination of —(C=O)—NR$^{19}$—* as $R^{17}$ and an organic group having a reactive functional group as $R^{18}$ are especially preferred.

In the solid-phase support of the present invention, a content ratio of the number of moles "a" of a reactive functional group contained in the above chain polymer and the number of moles "b" of the entire structural unit contained in the above chain polymer, (a/b), is from 0.03 to 0.25. By such a constitution, a ligand easily binds to the solid-phase support and nonspecific adsorption is suppressed.

The content ratio (a/b) is preferably 0.05 or more, more preferably 0.08 or more, further preferably 0.1 or more and especially preferably 0.13 or more in terms of allowing a ligand to easily bind to a support, and also preferably 0.23 or less and more preferably 0.22 or less in terms of suppressing nonspecific adsorption.

When the hydrophilic structural unit is a structural unit having a hydrophilic group, a content ratio of the number of moles "c" of the hydrophilic group contained in the above chain polymer and the number of moles "b" of the whole structural unit contained in the above chain polymer, (c/b), is preferably 0.1 or more, more preferably 0.3 or more and especially preferably 0.5 or more in terms of allowing a ligand to easily bind to a support, and also preferably 1.5 or less, more preferably 1.25 or less, further preferably 1 or less and especially preferably 0.9 or less in terms of easy polymer synthesis.

The above number of moles "a" is preferably 1 or more, more preferably 3 or more, further preferably 5 or more, especially preferably 10 or more, and also preferably 500 or less, more preferably 300 or less, further preferably 200 or less and especially preferably 100 or less.

The number of moles "b" is preferably 2 or more, more preferably 6 or more, further preferably 10 or more and especially preferably 20 or more, and also preferably 1,000 or less, more preferably 600 or less, further preferably 400 or less and especially preferably 250 or less.

The number of moles "c" is preferably 1 or more, more preferably 3 or more, further preferably 5 or more and especially preferably 10 or more, and also preferably 500 or less, more preferably 300 or less, further preferably 200 or less and especially preferably 150 or less.

The numbers of moles "a", "b" and "c" can be calculated by X-ray photoelectron spectroscopy, or from, for example, the weight of chain polymer binding to 1 g of a solid-phase support, the molecular weight of chain polymer and the amount of reactive functional group, and can be specifically measured in accordance with a method described in the examples mentioned below.

The chain polymer may have a structural unit other than the above structural unit constituting the first block and the structural unit constituting the second block, and a chain vinyl polymer is preferred and a diblock polymer is more preferred. In addition, a block is preferred in which the first block directly binds to the surface of a solid-phase support. It is preferred that the chain polymer be a diblock polymer represented by —(First block)—(Second block)— ( represents a binding position on the surface side of a solid-phase support).

In addition, one end of a chain polymer is not particularly limited as long as the end binds to the surface of a solid-phase support. It is however preferred that the one ends bind to the surface of a solid-phase support via a divalent linking group comprising a residual group of a polymerization initiating group. As the polymerization initiating group, a polymerization initiating group capable of living polymerization is preferred, a living radical polymerization initiating group is more preferred, an atom transfer radical polymerization initiating group and a reversible addition-fragmentation chain transfer polymerization initiating group are further preferred, and an atom transfer radical polymerization initiating group is especially preferred. Examples of the divalent linking group comprising a residual group of an atom transfer radical polymerization initiating group include a divalent group represented by the following formula (7-1) or (7-2).

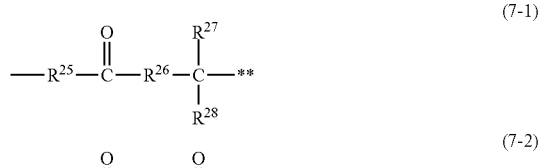
(7-1)

(7-2)

[In the above formula,
$R^{25}$ and $R^{29}$ represent —O— or —NH—,
$R^{26}$ and $R^{30}$ each independently represent a single bond or a phenylene group,
$R^{27}$ and $R^{28}$ each independently represent a hydrogen atom or an alkyl group, and
** represents a position bound to the end of a chain polymer.]

$R^{25}$ and $R^{29}$ are preferably —O—, and $R^{26}$ and $R^{30}$ are preferably a single bond, and $R^{27}$ and $R^{28}$ are preferably an alkyl group.

The number of carbons in the alkyl group represented by $R^{27}$ and $R^{28}$ is preferably from 1 to 8, more preferably from 1 to 4, and especially preferably 1 or 2. The alkyl group may be a straight chain or a branched chain, and specific examples thereof include, for example, a methyl group, an ethyl group, a n-propyl group, an isopropyl group, a n-butyl group, an isobutyl group, a sec-butyl group, a tert-butyl group, a pentyl group, a hexyl group, a heptyl group and an octyl group.

Meanwhile, the other end of a chain polymer is not particularly limited and a halogen atom is preferred. Examples of the halogen atom include, for example, a bromine atom, a chlorine atom and a fluorine atom.

In the solid-phase support of the present invention, a density of the above chain polymer occupying the surface of the solid-phase support is 0.1 polymers/nm$^2$ or more. That is, a polymer brush constituted from chain polymers is formed on the surface of a solid-phase support, and by the above constitution, a ligand easily binds thereto and nonspecific adsorption is suppressed.

The density occupied by the above chain polymer is preferably 0.3 polymers/nm$^2$ or more, more preferably 0.4 polymers/nm$^2$ or more, and further preferably 0.6 polymers/nm$^2$ or more in terms of suppressing nonspecific adsorption, in terms of the amount of bound ligand and in terms of achieving both an increase in sensitivity and a decrease in noise in detection, and also preferably 2 polymers/nm$^2$ or less, more preferably 1.6 polymers/nm$^2$ or less, and further preferably 1.2 polymers/nm$^2$ or less in terms of forming the polymer brush in an ease manner.

The density of the above chain polymer can be calculated, for example, by the following formula. Specifically, chain polymers are released from a solid-phase support by, for example, hydrolysis, and the density can be measured in accordance with a method described in the examples mentioned below.

Density of chain polymer (chain polymers/nm$^2$)=Number of chain polymers binding to 1 g of support (chain polymers)/Total surface area of 1 g of support (nm$^2$)

The number average molecular weight (Mn) of chain polymer is preferably from 1,000 to 100,000, more preferably from 3,000 to 50,000, and further more preferably from 5,000 to 30,000.

The weight average molecular weight (Mw) of chain polymer is preferably from 1,000 to 100,000, more preferably from 3,000 to 50,000, and especially preferably from 5,000 to 30,000.

In addition, the molecular weight distribution (Mw/Mn) is preferably from 1.0 to 2.5, more preferably from 1.0 to 2.0 and further preferably from 1.0 to 1.5 in terms of suppressing nonspecific adsorption and increasing the activity of a ligand bound to a solid-phase support.

The number average molecular weight and the weight average molecular weight mean average molecular weights in terms of polyethylene glycol, which are measured by gel permeation chromatography after releasing chain polymers from a solid-phase support by, for example, hydrolysis. The molecular weight of chain polymer before a reactive functional group is introduced is measured in a method as described in the examples mentioned below, and the number average molecular weight and the weight average molecular weight can be also calculated from such a molecular weight, the number of moles of a structural unit into which a reactive functional group is introduced, and the structure of a compound used for introducing a reactive functional group.

The portions other than a chain polymer constituting the solid-phase support of the present invention may be organic substances or inorganic substances such as metals and metal oxides, but not particularly limited thereto. It is preferred that the solid-phase support of the present invention contain a resin in addition to a chain polymer. As the resin, naturally-occurring polymers constituted of polysaccharides such as agarose, dextran and cellulose, or synthetic polymers may be used.

In addition, a form of the solid-phase support of the present invention is not particularly limited and may be any of, for example, beads, monoliths, films, fibers and chips, and beads are preferred and magnetic beads are more preferred in terms of ease in detection or separation of a target substance.

In the present description, the "magnetic beads" mean beads with a magnetic substance. The solid-phase support of the present invention has high water dispersibility even in the form of magnetic beads. In the case of the form of magnetic beads, the beads can be separated by, for example, a magnet without using, for example, a centrifuge, and thus the solid-phase support can be simply or automatically separated from a sample.

The magnetic substance may have any of ferromagnetism, paramagnetism and superparamagnetism, and is preferably superparamagnetic in terms of easing separation in a magnetic field and redispersion after removing the magnetic field. Examples of the magnetic substance include metals such as ferrite, iron oxide, iron, manganese oxide, manganese, nickel oxide, nickel, cobalt oxide and cobalt, or alloys.

Specific examples of the magnetic beads include those formed by binding the above chain polymer at least to the surface of any beads in the following (i) to (iv). Porous or non-porous magnetic polymer beads are preferred.

(i) Beads in which magnetic minute particles are dispersed in a continuous phase comprising a non-magnetic substance such as a resin, (ii) beads in which a secondary agglomerate of magnetic minute particles is constituted as a core and a non-magnetic substance such as a resin is constituted as a shell, (iii) beads in which mother beads having nuclear beads constituted from a non-magnetic substance such as a resin and a magnetic layer (secondary agglomerate layer) comprising magnetic minute particles provided to the surface of the nuclear beads are constituted as a core, and a non-magnetic layer such as a resin is provided to the outermost layer of the mother beads as a shell (hereinafter, referred to as the outermost layer shell), and (iv) beads in which magnetic minute particles are dispersed in the holes of porous beads comprising, for example, a resin and silica, in which a non-magnetic layer such as a resin may be provided to the outermost layer of beads as a shell.

The beads in (i) to (iv) are all known and can be produced in accordance with a conventional method.

Examples of the resins in the nuclear beads in (iii) above and the porous beads in (iv) above include resins derived from one or two or more monomers selected from the group consisting of a monofunctional monomer and a cross-linkable monomer.

Examples of the above monofunctional monomer include a monofunctional aromatic vinyl monomer such as styrene, α-methylstyrene and halogenated styrene; and a monofunctional (meth)acrylate monomer such as methyl (meth)acrylate, ethyl (meth)acrylate, stearyl (meth)acrylate, cyclohexyl (meth)acrylate and isobornyl (meth)acrylate.

Examples of the above multifunctional monomers include, for example, multifunctional aromatic vinyl monomers such as divinylbenzene; multifunctional (meth)acrylate monomers such as ethyleneglycol di(meth)acrylate, trimethylolpropane tri(meth)acrylate, dipentaerythritol hexa(meth)acrylate and allyl (meth)acrylate; and conjugated diolefins such as butadiene and isoprene.

In addition, as the resins in (i) and (ii) above as well as the resins in the outermost layer shell in (iii) and (iv) above, a resin having one or two or more functional groups selected from the group consisting of a glycidyl group, an amino group and a hydroxy group at least on the surface is preferred. The above functional groups may be introduced by the chemical modification of the resin surface, or by polymerization of monomer composition at least comprising one or two or more monomers having the above functional group. Examples of the above chemical modification include the formation of a hydroxy group by hydrolysis of a glycidyl group, and the formation of an amino group by reduction of a nitro group. As the above monomer composition having a functional group, monomer composition at least comprising a glycidyl group-containing monomer is more preferred (hereinafter, beads in which the resin in the above outermost layer shell is a resin formed by monomer composition at least comprising a glycidyl group-containing monomer are also referred to as a glycidyl group-containing magnetic beads). One or two or more monomers selected from the group consisting of the above monofunctional monomer and cross-linkable monomer may be further contained.

Examples of the glycidyl group-containing monomer include, for example, glycidyl (meth)acrylate and allyl glycidyl ether. Examples of the amino group-containing monomer include, for example, 2-aminoethyl (meth)acrylate. Examples of the hydroxy group-containing monomer include, for example, 1,4-cyclohexane dimethanol mono (meth)acrylate.

In addition, when the solid-phase support of the present invention is a bead, the average particle diameter (volume average particle diameter) is preferably from 0.1 to 500 µm, more preferably from 0.2 to 50 µm, and further preferably from 0.3 to 10 µM. Within such a range, when the solid-phase support is a magnetic bead, the magnetic collection speed becomes faster and handling properties are improved, and also the amount of bound ligand becomes larger, and detection sensitivity becomes higher. In addition, the coefficient of variation of the average particle diameter is only required to be about 20% or less.

The specific surface area is only required to be about from 1.0 to 2.0 m$^2$/g.

The above average particle diameter and specific surface area can be measured by, for example, laser diffraction scattering bead size distribution measurement.

<Method for Producing Solid-Phase Support>

The solid-phase support of the present invention can be produced by properly combining conventional methods. As the method for producing the solid-phase support of the present invention, a method comprising (Step 1) a step of preparing a support having a polymerization initiating group at least on the surface (hereinafter, also referred to as a polymerization initiating group-containing support), and (Step 2) a step of polymerizing a monomer from the polymerization initiating group is preferred, for example, in terms of highly increasing the density of chain polymer occupying the surface of the solid-phase support and further suppressing nonspecific adsorption, in terms of binding a chain polymer with a narrow molecular weight distribution to the solid-phase support and further suppressing nonspecific adsorption, and in terms of enhancing the function of a ligand binding to the solid-phase support.

Specific examples of the above production method include the following methods <PR-1> and <PR-2>. These methods will be described using a method for producing a solid-phase support to which a diblock polymer having a carboxy group, an amino group or a tosyl group as a reactive functional group (15) binds as an example.

<PR-1> A method comprising (Step 1) of preparing a polymerization initiating group-containing support, (Step 2-1-1) of polymerizing separately each of a hydrophilic monomer (11) and a monomer having a functional group into which a carboxy group, an amino group or a tosyl group can be introduced (12) (e.g. a hydroxy group, an epoxy group, an ester group, an amino group, a protected carboxylic group etc., the same shall apply hereinafter) from the polymerization initiating group, (Step 2-1-2) of introducing a carboxy group, an amino group or a tosyl group into a chain polymer introduced into a solid-phase support (14) by an addition reaction, a substitution reaction, a condensation reaction or a deprotection reaction.

<PR-2> A method comprising (Step 1) of preparing a polymerization initiating group-containing support, (Step 2-2-1) of obtaining a monomer having a carboxy group, an amino group or a tosyl group as a reactive functional group (13) by introducing a carboxy group, an amino group or a tosyl group into a monomer having a functional group into which a carboxy group, an amino group or a tosyl group can be introduced (12) by an addition reaction, a substitution reaction, a condensation reaction or a deprotection reaction, and (Step 2-2-2) of polymerizing separately each of this monomer (13) and the hydrophilic monomer (11) from the polymerization initiating group. When a monomer having a carboxy group, an amino group or a tosyl group is used, a support can be produced without the (step 2-2-1).

Examples of the monomer having a carboxy group, an amino group or a tosyl group include, for example, (meth)acrylic acid, (meth)acrylic acid salts and aminoethyl (meth)acrylate.

(Step 1)

A polymerization initiating group-containing support can be obtained, for example, by bringing a compound having a polymerization initiating group into contact with a support material having one or two or more groups selected from the group consisting of a hydroxy group, an amino group, an epoxy group and a carboxy group (hereinafter, these are collectively referred to as hydroxy group etc.) at least on the surface (hereinafter, also referred to as a support material) to convert a hydrogen atom contained in the above hydroxy group etc. into the polymerization initiating group (hereinafter, this reaction is also referred to as a polymerization initiating group introducing reaction). Among the above support materials, a support material having a hydroxy group at least on the surface can be obtained, for example, by bringing the above glycidyl group-containing magnetic beads into contact with an acid such as inorganic acid or an organic acid to conduct a ring-opening of the glycidyl group.

A polymerization initiating group-containing support can be also obtained by polymerizing monomer composition comprising a monomer having a polymerization initiating group. Examples of the monomer having a polymerization initiating group include, for example, 2-(2-bromoisobutyryloxy)ethyl methacrylate.

As the above compound having a polymerization initiating group, a compound having a polymerization initiating group capable of living polymerization is preferred, a compound having a living radical polymerization initiating group is more preferred, a compound having an atom transfer radical polymerization initiating group and a compound having a reversible addition-fragmentation chain transfer polymerization initiating group are further preferred, and a compound having an atom transfer radical polymerization initiating group is especially preferred. Examples of the compound having an atom transfer radical polymerization initiating group include, for example, 2-bromoisobutyryl bromide, 4-(bromomethyl)benzoic acid, ethyl 2-bromoisobutyrate, 2-bromopropionyl bromide and tosyl chloride.

In the polymerization initiating group introducing reaction, a total amount of compound having a polymerization initiating group used is normally about from 0.001 to 100 times by mass and preferably about from 0.01 to 50 times by mass with respect to a support material.

It is preferred that the polymerization initiating group introducing reaction be carried out in the presence of a basic catalyst such as triethylamine, N,N-dimethyl-4-aminopyridine, diisopropylethylamine or pyridine. One of these basic catalysts may be used alone or two or more of these basic catalysts may be used in combination.

The total amount of basic catalyst used is normally about from 1 to 10 molar equivalents and preferably about from 1 to 5 molar equivalents with respect to a compound having a polymerization initiating group.

It is also preferred that the polymerization initiating group introducing reaction be carried out in the presence of a solvent. Examples of solvents include ether solvents such as tetrahydrofuran, 1,4-dioxane and 1,3-dioxane; and aprotic solvents such as dimethylformamide and dimethylsulfoxide, and one of these solvents can be used alone or two or more of these solvents can be used in combination.

In addition, the reaction time of the polymerization initiating group introducing reaction is normally about from 30 minutes to 24 hours, and the reaction temperature may be properly selected from the boiling point of a solvent or lower.

(Step 2-1-1)

The polymerization method for the polymerization reaction in the step 2-1-1 may be selected depending on a kind of polymerization initiating group, and living polymerization is preferred, living radical polymerization is more preferred, atom transfer radical polymerization (ATRP polymerization) and reversible addition-fragmentation chain transfer polymerization (RAFT polymerization) are further preferred, and atom transfer radical polymerization is especially preferred in terms of simply and easily obtaining a target product. By polymerization by atom transfer radical polymerization, a chain polymer can be allowed to simply bind to a wide variety of supports. Furthermore, biocompatibility, high compressive elasticity, low frictional characteristics and size exclusion characteristics are imparted to a solid-phase support thus obtained, and the density of chain polymer occupying the surface of a solid-phase support is increased, and thus nonspecific adsorption is suppressed.

Examples of the monomer (11) are, for example, a monomer having a hydroxy group, a monomer having a polyoxyethylene group, a monomer having a group having a zwitterion, a monomer having a phosphate group, and further monomers having hydrophilicity such as dimethyl (meth) acrylamide, dimethylaminopropyl (meth)acrylamide, isopropyl (meth)acrylamide and diethyl (meth)acrylamide.

Examples of the monomer having a hydroxy group are, for example, 2-hydroxyethyl (meth)acrylate, 2-hydroxyethyl (meth)acrylamide, 2-hydroxypropyl (meth)acrylate, 2-hydroxypropyl (meth)acrylamide, 2-hydroxybutyl (meth)acrylate, 2-hydroxybutyl (meth)acrylamide, glycerol 1-(meth)acrylate and glycerol 1-(meth)acrylamide. Examples of the monomer having a polyoxyethylene group are, for example, methoxypolyethylene glycol mono(meth)acrylate and methoxypolyethylene glycol mono(meth)acrylamide. Examples of the monomer having a group having a zwitterion are, for example, [2-((meth)acryloyloxy)ethyl](carboxylatomethyl)dimethylamineium, [2-((meth)acryloyloxy)ethyl](carboxylatoethyl)dimethylamineum, [2-((meth)acryloyloxy)ethyl](carboxylatopropyl)dimethylamineium, [2-((meth)acryloyloxy)ethyl]dimethyl-(3-sulfomethyl)ammonium hydroxide, [2-((meth)acryloyloxy]ethyl]dimethyl-(3-sulfoethyl)ammonium hydroxide, [2-((meth)acryloyloxy)ethyl]dimethyl-(3-sulfopropyl)ammonium hydroxide, and O-[2-((meth)acryloyloxy)ethoxy(oxylato)phosphinyl] choline. Examples of the monomer having a phosphate group are, for example, 2-phosphoric ethyl (meth)acrylate and 2-phosphoric ethyl (meth)acrylamide.

One of these monomers may be used alone or two or more of these monomers may be used in combination.

Examples of the monomer (12) include, for example, N-hydroxysuccinimide (meth)acrylate, N-hydroxysuccinimide (meth)acrylamide, 2-hydroxyethyl (meth)acrylamide, 2-hydroxyethyl (meth)acrylate, glycidyl (meth)acrylate, aminoethyl (meth)acrylate and tert-butyl (meth)acrylate. One of these monomers may be used alone or two or more of these monomers may be used in combination.

The total amounts of monomers (11) and (12) used each are normally about from 5 to 10,000 molar equivalents and preferably about from 10 to 5,000 molar equivalents with respect to a polymerization initiating group binding to the surface of a support.

When the polymerization reaction in the step 2-1-1 is carried out by atom transfer radical polymerization, it is preferred that the reaction be carried out in the presence of a transition metal compound and a ligand in terms of reaction efficiency.

As the transition metal compound, a copper compound is preferred. Examples of the copper compound include, for example, halogenated copper such as copper(I) bromide, copper(II) bromide, copper(I) chloride and copper(II) chloride, and further copper(I) triflate and copper(II) triflate. One of these compounds may be used alone or two or more of these compounds may be used in combination. The total amount of transition metal compound used is normally about from 1 to 10,000 ppm in the reaction system.

As the ligand, a ligand comprising two or more nitrogen atoms in the same molecule is preferred. Examples of the ligand comprising two or more nitrogen atoms in the same molecule include, for example, tris(2-pyridylmethyl)amine, bipyridine, bipyridine derivatives and tris[2-(dimethylamino)ethyl]amine. One of these ligands may be used alone or two or more of these ligands may be used in combination.

The total amount of ligand used is normally about from 0.5 to 10 molar equivalents with respect to a transition metal compound.

It is also preferred that the polymerization reaction in the step 2-1-1 be carried out in the presence of a reducing agent and a solvent in terms of reaction efficiency.

Examples of reducing agents include, for example, ascorbic acid, glucose, hydrazine and copper, and one of these reducing agents can be used alone or two or more of these reducing agents can be used in combination.

Examples of solvents include, for example, water; amide solvents such as dimethylformamide; alcohol solvents such as methanol and ethanol; and ether solvents such as anisole, and one of these solvents can be used alone or two or more of these solvents can be used in combination.

The pH in the reaction system of the polymerization reaction is preferably from 3 to 10. The reaction time of the polymerization reaction is normally about from 30 minutes to 12 hours, and the reaction temperature may be properly selected from the boiling point of a solvent or lower. The polymerization reaction proceeds even under mild conditions of about from 25 to 60° C.

(Step 2-1-2)

The step 2-1-2 is the step of introducing a carboxy group, an amino group or a tosyl group into a chain polymer introduced into a solid-phase support (14) by an addition reaction, a substitution reaction, a condensation reaction or a deprotection reaction.

Examples of methods for introducing a carboxy group include, for example, a method in which using a monomer having a hydroxy group or an amino group as the monomer (12), a chain polymer thus obtained (14) is subjected to an addition reaction with carboxylic anhydride, a method in which using a monomer having an epoxy group as the monomer (12), a chain polymer thus obtained (14) is hydrolyzed to form a hydroxy group and then subjected to an addition reaction with carboxylic anhydride, a method in which using a monomer having an epoxy group as the monomer (12), a chain polymer thus obtained (14) is subjected to an addition reaction with a compound having a nucleophilic group such as a mercapto group or an amino group and a carboxy group, and a method in which using a monomer having a protected carboxy group as the monomer (12), a chain polymer thus obtained (14) is deprotected.

Examples of carboxylic anhydride include, for example, succinic anhydride, maleic anhydride, glutaric anhydride, phthalic anhydride and hexahydrophthalic anhydride. Among these, succinic anhydride is preferred in terms of easy progression of the reaction with a hydroxy group and an amino group. The total amount of, for example, carboxylic anhydride used is normally about from 0.1 to 2000 molar equivalents and preferably from 1 to 1000 molar equivalents with respect to a structural unit derived from the monomer (12).

Examples of the compound having a nucleophilic group such as a mercapto group or an amino group and a carboxy group include mercaptopropionic acid and amino acids. Examples of the monomer having a protected carboxy group include tert-butyl (meth)acrylate and N-hydroxysuccinimide (meth)acrylate. The deprotection method can be carried out by a well-known method depending on protecting groups, and examples thereof include, for example, hydrolysis.

Examples of methods for introducing an amino group include a method in which using a monomer having an epoxy group as the monomer (12), a chain polymer thus obtained (14) is subjected to an addition reaction with ammonia or a compound having two or more amino groups. Examples of the compound having two or more amino groups include ethylenediamine.

Examples of methods for introducing a tosyl group include, for example, a method in which using a monomer having a hydroxy group or an amino group as the monomer (12), tosyl chloride is added to a chain polymer thus obtained (14), and a method in which using a monomer having an epoxy group as the monomer (12), a chain polymer thus obtained (14) is hydrolyzed to form a hydroxy group and tosyl chloride is then added.

It is preferred that the step 2-1-2 be likewise carried out in the presence of the basic catalyst and solvent as in the step 1. The reaction time of the step 2-1-2 is normally about 30 minutes to 24 hours, and the reaction temperature may be properly selected from the boiling point of a solvent or lower.

The step 2-2-1 may be carried out in accordance with the step 2-1-2, and the step 2-2-2 may be carried out in accordance with the step 2-1-1.

In the solid-phase support of the present invention obtained as above, a ligand easily binds to a reactive functional group and nonspecific adsorption is suppressed. Since a chain polymer is a block polymer, a ligand such as an antibody easily binds thereto, and both an increase in sensitivity and a decrease in noise in detection using antigen-antibody reactions are easily achieved. The reason why such an effect is achieved is not necessarily clear; however, the present inventors consider the reason is that, since in the case of a block polymer, a reactive functional group locally exists, an antibody easily binds thereto and a higher order structure such as a sandwich structure (primary antibody-antigen-secondary antibody) is easily taken.

Therefore, affinity supports obtained from the solid-phase support of the present invention can be widely used, for example, for in vitro diagnoses and researches in the biochemistry field, including, for example, immunoassay using antigen-antibody reactions such as enzyme immunoassay, radioimmunoassay and chemiluminescence immunoassay; the detection of, for example, proteins and nucleic acids; bioseparation of bio-related materials such as cells, proteins and nucleic acids; drug seeking; and biosensors. The solid-phase support of the present invention is especially suitable for use for immunoassay or detecting nucleic acids.

<Ligand-Binding Solid-Phase Support>

The ligand-binding solid-phase support of the present invention is formed by binding a ligand to the solid-phase support of the present invention.

The above ligand is only required to be a molecule which binds to a target substance, and examples thereof include, for example, antibodies; antigens; nucleic acids such as DNA and RNA; nucleotides; nucleosides; proteins such as Protein A, Protein G, (strept)avidin, enzymes and lectins; peptides such as insulin; amino acids; saccharides or polysaccharides such as heparin; lipids; vitamins such as biotin; medicine; substrates; hormones; and neurotransmitters.

Among these ligands, antibodies and antigens are preferred in terms of obtaining a ligand-binding solid-phase support suitable for, for example, diagnostic agents. The antibodies and antigens are only required to bind to a target substance, and examples thereof include antibodies for coagulation fibrinolysis tests such as anti-antiplasmin antibody, anti-D dimer antibody, anti-FDP antibody, anti-tPA antibody, anti-thrombin-antithrombin complex antibody and anti-FPA antibody or antigens thereof; antibodies for tumor tests such as anti-BFP antibody, anti-CEA antibody, anti-AFP antibody, anti-TSH antibody, anti-ferritin antibody and anti-CA19-9 antibody or antigens thereof; antibodies for serum protein tests such as anti-apolipoprotein antibody, anti-β-microglobulin antibody, anti-α1-microglobulin antibody, anti-immunoglobulin antibody and anti-CRP antibody or antigens thereof; antibodies for endocrine function tests such as anti-HCG antibody or antigens thereof; antibodies for medicine analyses such as anti-digoxin antibody and anti-lidocaine antibody or antigens thereof; antigens for infectious disease tests such as HBs antigen, HCV antigen, HIV-1 antigen, HIV-2 antigen, HTLV-1 antigen, *mycoplasma* antigen, *toxoplasma* antigen and streptolysin O antigen or antibodies thereof; and antigens for autoimmune tests such as DNA antigen and heat-aggregated human IgG or antibodies thereof. The antibodies may be polyclonal antibodies or monoclonal antibodies.

The binding of ligands may be carried out in accordance with a conventional method, and is preferably carried out by a covalent binding method. For example, when a reactive functional group is a carboxy group and a ligand has an amino group, binding may be carried out using a dehydration-condensation agent.

The ligand-binding solid-phase support of the present invention can be widely used for, for example, in vitro diagnosis and researches in the biochemistry field. The ligand-binding solid-phase support of the present invention is especially suitable for use for immunoassay or detecting nucleic acids.

<Method for Detecting or Separating Target Substance>

The method for detecting or separating a target substance in a sample according to the present invention is characterized by using the ligand-binding solid-phase support of the present invention.

The target substance is not limited as long as it binds to a ligand, and specific examples thereof include antigens; antibodies such as monoclonal antibodies and polyclonal antibodies; cells (normal cells, and cancer cells such as colon cancer cells and circulating cancer cells in blood); nucleic acids such as DNA and RNA; bio-related materials such as proteins, peptides, amino acids, saccharides, polysaccharides, lipids and vitamins, and the target substances may be small molecular compounds such as a drug as a target for drug discovery and biotin. The target substance may be labeled by, for example, a fluorescent substance.

The sample is not limited as long as it comprises the above target substance or has the possibility of comprising a target substance, and are specifically, for example, blood, blood plasma, blood serum and buffer solutions containing a target substance.

The method of detection or separation according to the present invention may be carried out in accordance with a conventional method, except that the ligand-binding solid-phase support of the present invention is used. Examples thereof include a method comprising a step of bringing the ligand-binding solid-phase support of the present invention into contact with a sample comprising a target substance by, for example, mixing (contact step), and a step of separating the ligand-binding solid-phase support which has grasped the target substance from the sample using, for example, a magnet (separation step). After such a separation step, a step of detecting the target substance or a step of dissociating the ligand and the target substance may be included.

EXAMPLES

The present invention will now be described in detail by way of examples thereof. It should be noted, however, that the present invention is not limited to these examples. Each analysis condition in the examples is as described below.

<Measurement of Molecular Weight of Chain Polymer>

The molecular weight of chain polymer was measured after releasing chain polymers from beads by hydrolysis using an aqueous solution of sodium hydroxide.

That is, 1 g of beads was dispersed in 4 g of an aqueous solution of sodium hydroxide (1 N, pH 14), and the obtained mixture was stirred at 25° C. for 3 hours to release chain polymers from beads. The beads were separated using magnetism, and the supernatant in which the chain polymers had been dissolved was collected. Next, to this chain polymer solution was added 1 M hydrochloric acid until the pH of the solution became 7 to neutralize the solution. In order to be used in calculating the weight of chain polymer, the weight of sodium chloride thus produced was calculated from the weight of 1 M hydrochloric acid added. The solution after neutralization was freeze-dried to obtain the chain polymer comprising sodium chloride as powders. In order to be used in calculating the weight of chain polymer, the weight of powder was measured.

The above powders were used as a test specimen, and the Mn and Mw of chain polymer formed on the surface of beads were measured under the following conditions by gel permeation chromatography (GPC) using TSKgel G3000PWXL column manufactured by Tosoh Corporation and ChromNAV chromatography data station program manufactured JASCO International Co., Ltd.

(Measurement Conditions)

Flow rate: 0.8 mL/min

Eluting solvent: 0.2 M sodium phosphate buffer (pH 7.0)

Column temperature: 25° C.

Reference material: TSKgel standard Poly (ethylene oxide) SE-kit manufactured by Tosoh Corporation and Polyethylene Glycol 4,000 manufactured by Wako Pure Chemical Industries, Ltd.

<Polymer Density of Chain Polymer Occupying Surface of Beads>

The polymer density was calculated from the weight of chain polymer released from beads, the number average molecular weight of chain polymer and the surface area of beads by the following formula.

[Density of chain polymer occupying surface of beads (chain polymers/nm$^2$)]=[Number of chain polymers binding to 1 g of beads (chain polymers)]/[Total surface area per g of beads (nm$^2$)]

Note that the methods for calculating the number of chain polymers binding to 1 g of beads and the total surface area per g of beads are as described below.

(Number of Chain Polymers Binding to 1 g of Beads)

The weight of chain polymer binding to 1 g of beads was calculated by the following formula ($\alpha$), and using the obtained value, the number of chain polymers binding to 1 g of beads was calculated by the following formulae ($\beta$) and ($\gamma$):

weight of chain polymer binding to 1 g of beads (mg)=weight of powder after freeze-drying (mg)−weight of sodium chloride (mg), ($\alpha$):

number of chain polymers binding to 1 g of beads (mol)={weight of chain polymer binding to 1 g of beads (mg)/number average molecular weight of chain polymer (g/mol)}/1000, ($\beta$):

and number of chain polymers binding to 1 g of beads (chain polymers)=number of chain polymers binding to 1 g of beads (mol)×6.02×10$^{23}$ (Avogadro's number). ($\gamma$):

(Total Surface Area Per g of Beads)

The total surface area was calculated by the following formulae ($\delta$) to ($\theta$). The specific gravity of beads in the formula ($\epsilon$) was calculated from the specific gravity of a polymer, the specific gravity of a magnetic substance, and the ratio of the polymer and the magnetic substance occupying beads:

volume per bead (μm$^3$)=4/3×π×{volume average radius of beads (μm)}$^3$, ($\delta$):

mass per bead (g)=volume per bead (μm$^3$)×specific gravity of beads (g/μm$^3$), ($\epsilon$):

number of beads per g of beads (beads)=1 g/mass per bead (g), ($\zeta$):

surface area per bead (nm$^2$)=4×π×{radius of bead (nm)}$^2$, ($\eta$):

and total surface area per g of beads (nm$^2$)=surface area per bead (nm$^2$)×number of beads per g of beads (beads). ($\theta$):

<Content of Reactive Functional Group>

The content of reactive functional group per g of solid content in beads was obtained by measuring the content of reactive functional group (carboxy group) contained in chain polymers released from beads using conductometry (Metrohm, 794 Basic Titrino).

<Number of Moles "a", "b" and "c">

The number of moles "a" and the number of moles "c" were calculated by the following method. The number of moles "a" and the number of moles "c" were added up to calculate the number of moles "b".

(Number of Moles "a")

Number of moles "a"=amount of reactive functional group per g of beads (mol)/number of polymers per g of beads (polymers)

(Number of Moles "c")

The number of moles "c" was calculated from the following formulae (A), (B) and (C):

weight per g of beads in structural unit constituting second block (g)=amount of reactive functional group per g of beads (mol)×molecular weight of structural unit constituting second block (g/mol) (A):

weight per g of beads in structural unit constituting first block (g)=weight of chain polymer per g of beads (g)−weight per g of beads in structural unit constituting second block (g), (B):

and number of moles "c"={weight per g of beads in structural unit constituting first block (g)/molecular weight of structural unit constituting first block (g/mol)}/number of polymers per g of beads (polymers). (C):

<Volume Average Particle Diameter>

The volume average particle diameter of the beads was measured by a laser diffraction scattering bead size distribution measuring device (Beckman Coulter LS13 320).

Synthetic Example 1

Synthesis of Magnetic Beads Having Hydroxy Group on Surface

With 20 g of a 1 mass % aqueous solution of dodecyl sodium sulfate, 2 g of a 75% solution of di(3,5,5-trimethyl hexanoyl)peroxide ("PEROYL 355-75 (S)" manufactured by NOF Corporation) was mixed, and the obtained mixture was finely emulsified by an ultrasonic disperser. This was put into a reactor comprising 13 g of polystyrene beads (number average particle diameter: 0.77 μm) and 41 g of water, and the mixture was stirred at 25° C. for 12 hours.

Next, 96 g of styrene and 4 g of divinyl benzene were emulsified with 400 g of a 0.1 mass % aqueous solution of dodecyl sodium sulfate in another container, and this was put into the above reactor, and the mixture was stirred at 40° C. for 2 hours, followed by raising the temperature to 75° C., and polymerization was carried out for 8 hours. After cooling to room temperature, only beads taken out by centrifugation were washed with water and dried. These beads were used as nuclear beads (number average particle diameter: 1.5 μm).

Next, acetone was added to oily magnetic fluid ("EXP series, EMG", manufactured by Ferrotec Corporation) in another container to precipitate and deposit beads, and these were then dried to obtain ferrite magnetic minute particles having the surface hydrophobized (average primary particle diameter: 0.01 μm).

Next, 15 g of the above nuclear beads and 15 g of the above hydrophobized magnetic minute particles were mixed well by a mixer, and this mixture was treated using an NHS-0 type hybridization system manufactured by Nara Machinery Co., Ltd. at a circumferential velocity of wings (impeller) of 100 m/sec (16,200 rpm) for 5 minutes to obtain mother beads having a magnetic layer comprising the magnetic minute particles on the surface (number average particle diameter: 2.0 μm).

Next, 250 g of a 0.50 mass % aqueous solution of dodecyl sodium sulfate was charged into a 500 mL separable flask, and then 10 g of the above mother beads having a magnetic layer were added, and the obtained mixture was dispersed by a homogenizer and then heated to 60° C., and the temperature was maintained.

Next, 75 g of a 0.50 mass % aqueous solution of dodecyl sodium sulfate, 13.5 g of methyl methacrylate (hereinafter, referred to as "MMA"), 1.5 g of trimethylolpropane trimethacrylate (hereinafter, referred to as "TMP"), and 0.3 g of a 75% solution of di(3,5,5-trimethyl hexanoyl)peroxide ("PEROYL 355-75 (S)" manufactured by NOF Corporation) were put into another container and dispersed to obtain a pre-emulsion. The total amount of this pre-emulsion was added dropwise to the above 500 mL separable flask maintained at 60° C. over a period of two hours. After a dropwise addition, this was maintained at 60° C. and the mixture was stirred for an hour.

After that, 37.5 g of a 0.50 mass % aqueous solution of dodecyl sodium sulfate, 6.56 g of glycidyl methacrylate (hereinafter, referred to as "GMA"), 0.94 g of TMP, and 0.15 g of a 75% solution of di(3,5,5-trimethyl hexanoyl)peroxide ("PEROYL 355-75 (S)" manufactured by NOF Corporation) were put into another container and dispersed to obtain a pre-emulsion. The total amount of this pre-emulsion was added dropwise to the above 500 mL separable flask maintained at 60° C. over a period of an hour and 20 minutes. After that, the temperature was elevated to 75° C. and polymerization was then continued for another two hours, and the reaction was completed. Subsequently, 10 mL of a 1 mol/L aqueous solution of sulfuric acid was put into this 500 mL separable flask and the mixture was stirred at 60° C. for 6 hours. Next, the beads in the above 500 mL separable flask were separated using magnetism and then repeatedly washed with distilled water.

As described above, the magnetic beads having hydroxy groups on the surface were obtained.

Synthetic Example 2

Synthesis of Magnetic Beads having Atom Transfer Radical Polymerization Initiating Group on Surface (1)

Into a flask, 10 g of magnetic beads having hydroxy groups on the surface, obtained in Synthetic Example 1, were charged, and 32 mL of dehydrated tetrahydrofuran and 7.5 mL of triethylamine were added under a nitrogen flow and the mixture was stirred. This flask was soaked in an ice bath, and thereto was added 6.3 mL of 2-bromoisobutyryl bromide dropwise over a period of 30 minutes. After a reaction at room temperature for 6 hours, the beads in the flask were separated using magnetism, and the beads were then redispersed in acetone. The magnetic separation and redispersion were carried out another several times, and the beads were then dispersed in a 0.10 mass % aqueous solution of dodecyl sodium sulfate. Br contained in the atom transfer radical polymerization initiating group (2-bromoisobutyryl group) was detected by a fluorescent X-ray analysis.

As described above, the magnetic beads having the atom transfer radical polymerization initiating group (2-bromoisobutyryl group) on the surface were obtained. These beads were used as beads (A).

Synthetic Example 3

Synthesis of Magnetic Beads having Atom Transfer Radical Polymerization Initiating Group on Surface (2)

Into a flask, 10 g of magnetic beads having hydroxy groups on the surface, obtained in Synthetic Example 1, were charged, and 32 mL of dehydrated tetrahydrofuran and 0.4 mL of triethylamine were added under a nitrogen flow and the mixture was stirred. This flask was soaked in an ice bath, and 0.2 mL of 2-bromoisobutyryl bromide was added. After a reaction at room temperature for 6 hours, the beads in the flask were separated using magnetism, and the beads were then redispersed in acetone. The magnetic separation and redispersion were carried out another several times, and the beads were then dispersed in a 0.10 mass % aqueous solution of dodecyl sodium sulfate. Br contained in the atom transfer radical polymerization initiating group (2-bromoisobutyryl group) was detected by a fluorescent X-ray analysis.

As described above, the magnetic beads having the atom transfer radical polymerization initiating group (2-bromoisobutyryl group) on the surface were obtained. These beads are used as beads (B).

Synthetic Example 4

Synthesis of Magnetic Beads having Atom Transfer Radical Polymerization Initiating Group on Surface (3)

Into a flask, 10 g of magnetic beads having hydroxy groups on the surface, obtained in Synthetic Example 1, were charged, and 32 mL of dehydrated tetrahydrofuran and 0.2 mL of triethylamine were added under a nitrogen flow and the mixture was stirred. This flask was soaked in an ice bath, and 0.1 mL of 2-bromoisobutyryl bromide was added dropwise over a period of 30 minutes. After a reaction at room temperature for 6 hours, the beads in the flask were separated using magnetism, and the beads were then redispersed in acetone. The magnetic separation and redispersion were carried out another several times, and the beads were then dispersed in a 0.10 mass % aqueous solution of dodecyl sodium sulfate. Br contained in the atom transfer radical polymerization initiating group (2-bromoisobutyryl group) was detected by a fluorescent X-ray analysis.

As described above, the magnetic beads having the atom transfer radical polymerization initiating group (2-bromoisobutyryl group) on the surface were obtained. These beads are used as beads (C).

Example 1

(1) The chain polymer propagation reaction was carried out in accordance with the following synthetic route.

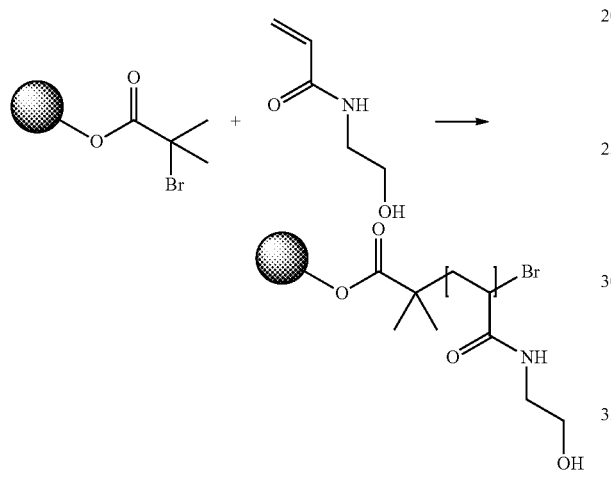

That is, 2 g of the beads (A) obtained in Synthetic Example 2 were dispersed in 6 mL of a sodium phosphate buffer (50 mM, pH 7.8), and 0.5 g of 2-hydroxyethyl acrylamide (hereinafter, referred to as "HEAA") and 0.40 mL of a mixed aqueous solution of 0.05 mol/L tris(2-pyridylmethyl)amine and 0.05 mol/L copper(II) bromide were added thereto.

Subsequently, 1.0 mL of a 0.2 mol/L aqueous solution of L-ascorbic acid was added thereto and a stopper was sealed to start the reaction. After stirring at 45° C. for 4 hours, the stopper was opened to stop the reaction by an exposure to air. The beads were separated using magnetism to remove, for example, unreacted monomers and catalysts.

(2) Next, the chain polymer propagation reaction was carried out in accordance with the following synthetic route and the ester bond of poly(N-hydroxysuccinimide methacrylate)block was hydrolyzed.

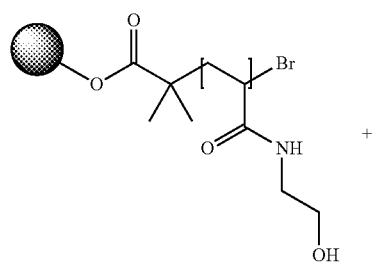

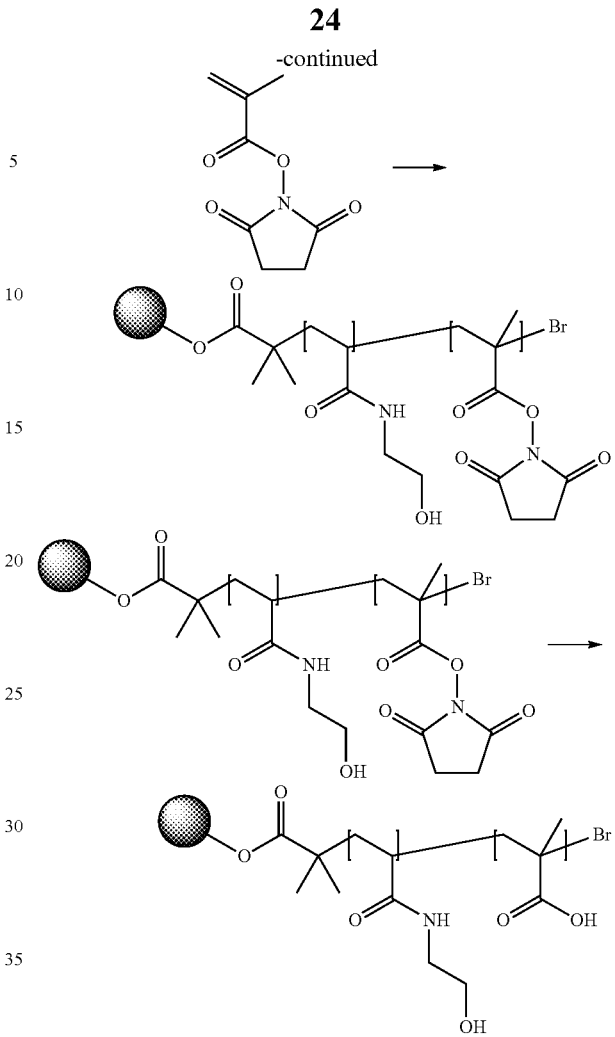

That is, the beads obtained above were dispersed in 6 mL of anisole, and 0.5 g of N-hydroxysuccinimide methacrylate and 0.40 mL of a mixed anisole solution of 0.05 mol/L tris(2-pyridylmethyl)amine and 0.05 mol/L copper(II) bromide were added thereto. Subsequently, 1.0 mL of a 0.2 mol/L anisole solution of L-ascorbic acid was added thereto and a stopper was sealed to start the reaction. After stirring at 45° C. for an hour, the stopper was opened to stop the reaction by an exposure to air. The beads were separated using magnetism to remove, for example, unreacted monomers and catalysts.

Next, 10 mL of water was added and the mixture was stirred at 25° C. for 12 hours.

As described above, the magnetic beads 1 in which a block copolymer of HEAA and methacrylic acid (hereinafter, referred to as "MAA") binds to the surface (volume average particle diameter: 3.0 μm) were obtained. The Mn, Mw and Mw/Mn of the block copolymer of HEAA and MAA, and the polymer density of the block copolymer were measured. In addition, the content of reactive functional group (carboxy group) and the numbers of moles "a", "b" and "c" were measured.

The measurement results are shown in Table 1.

Example 2

The magnetic beads 2 in which a block copolymer of HEAA and MAA binds to the surface (volume average particle diameter: 3.0 μm) were obtained in the same operations as in Example 1, except that the reaction time of the chain polymer propagation reaction to propagate the chain polymer using N-hydroxysuccinimide methacrylate was changed to an hour to 30 minutes.

The results of each measurement carried out in the same manner as in Example 1 are shown in Table 1.

Example 3

The magnetic beads 3 in which a block copolymer of HEAR and MAA binds to the surface (volume average particle diameter: 3.0 μm) were obtained in the same operations as in Example 1, except that the reaction time of the chain polymer propagation reaction to propagate the chain polymer using N-hydroxysuccinimide methacrylate was changed to an hour to 15 minutes.

The results of each measurement carried out in the same manner as in Example 1 are shown in Table 1.

Example 4

(Chain Polymer Propagation Reaction (1))
The chain polymer propagation reaction was carried out in accordance with the following synthetic route.

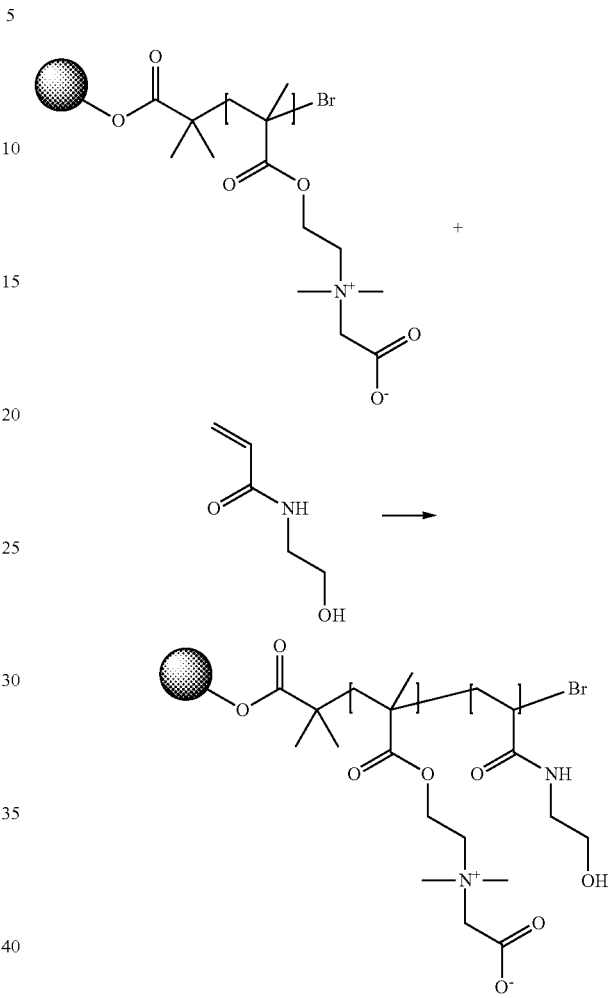

That is, 2 g of the beads (A) obtained in Synthetic Example 2 was dispersed in 6 mL of a sodium phosphate buffer (50 mM, pH 7.8), and 0.5 g of [2-(methacryloyloxy)ethyl] (carboxylatomethyl)dimethylaminium (hereinafter, referred to as "CBMA") and 0.40 mL of a mixed aqueous solution of 0.50 mol/L tris(2-pyridylmethyl)amine and 0.05 mol/L copper(II) bromide were added thereto. Subsequently, 1.0 mL of a 0.2 mol/L aqueous solution of L-ascorbic acid was added thereto and a stopper was sealed to start the reaction. After stirring at 45° C. for 4 hours, the stopper was opened to stop the reaction by an exposure to air. The beads were separated using magnetism to remove, for example, unreacted monomers and catalysts.

(Chain Polymer Propagation Reaction (2))
Next, the chain polymer propagation reaction was carried out in accordance with the following synthetic route.

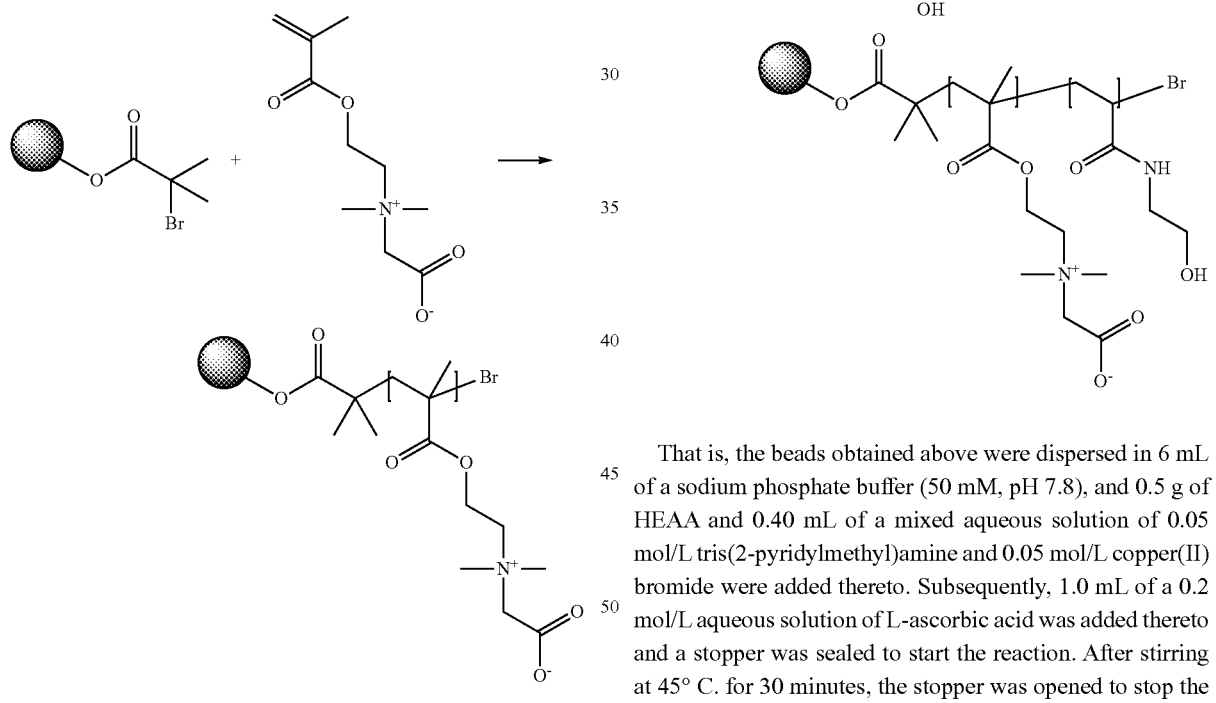

That is, the beads obtained above were dispersed in 6 mL of a sodium phosphate buffer (50 mM, pH 7.8), and 0.5 g of HEAA and 0.40 mL of a mixed aqueous solution of 0.05 mol/L tris(2-pyridylmethyl)amine and 0.05 mol/L copper(II) bromide were added thereto. Subsequently, 1.0 mL of a 0.2 mol/L aqueous solution of L-ascorbic acid was added thereto and a stopper was sealed to start the reaction. After stirring at 45° C. for 30 minutes, the stopper was opened to stop the reaction by an exposure to air. The beads were separated using magnetism to remove, for example, unreacted monomers and catalysts, and the magnetic beads in which a block copolymer of CBMA and HEAA binds to the surface were thus obtained. The Mn, Mw and Mw/Mn of the block copolymer of CBMA and HEAA and the polymer density of the block copolymer were measured. The measurement results are shown in Table 1.

(Condensation Reaction)
Next, the condensation reaction was carried out in accordance with the following synthetic route.

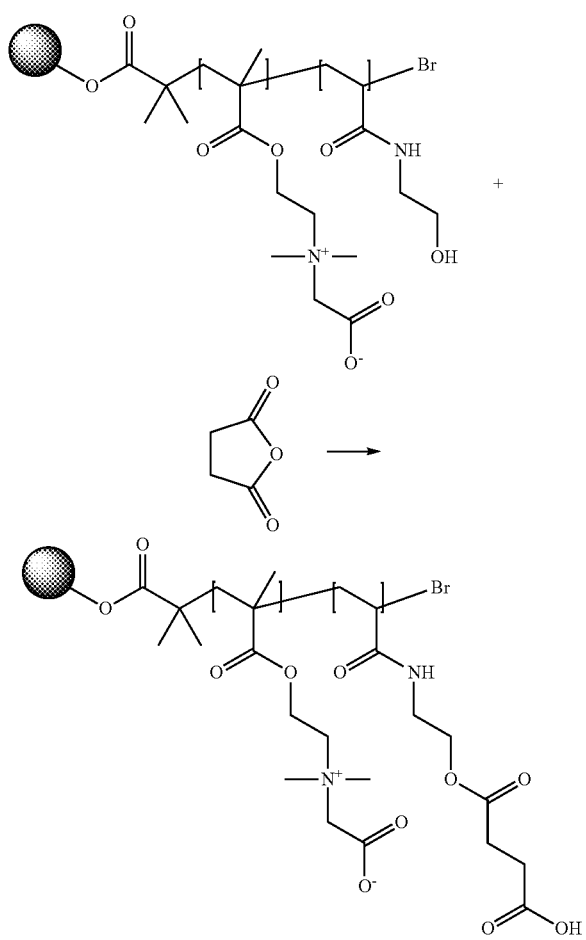

That is, 1.5 g of the beads obtained above were dispersed in 8 mL of dimethylsulfoxide (DMSO), and 7.2 mL of a DMSO solution in which 1.5 g of succinic anhydride was dissolved and 0.3 mL of triethylamine were added thereto to start the reaction. After stirring at 25° C. for 4 hours, the beads were separated using magnetism to remove excess raw materials.

As described above, the magnetic beads 4 in which the hydroxy group at the end of HEAA was converted into a reactive functional group (carboxy group) (volume average particle diameter: 3.0 μm) were obtained. The content of reactive functional group (carboxy group) and the numbers of moles "a", "b" and "c" were measured. The measurement results are shown in Table 1.

Example 5

The magnetic beads 5 in which a block copolymer of HEAA and MAA binds to the surface (volume average particle diameter: 3.0 μm) were obtained in the same operations as in Example 1, except that the beads (A) were changed to the beads (B) obtained in Synthetic Example 3.

The results of each measurement carried out in the same manner as in Example 1 are shown in Table 1.

Comparative Example 1

The magnetic beads 6 in which a block copolymer of HEAA and MAA binds to the surface (volume average particle diameter: 3.0 μm) were obtained in the same operations as in Example 1, except that the reaction time of the chain polymer propagation reaction to propagate the chain polymer using N-hydroxysuccinimide methacrylate was changed from an hour to 3 hours.

The results of each measurement carried out in the same manner as in Example 1 are shown in Table 1.

Comparative Example 2

The magnetic beads 7 in which a block copolymer of HEAA and MAA binds to the surface (volume average particle diameter: 3.0 μm) were obtained in the same operations as in Example 1, except that the amount of N-hydroxysuccinimide methacrylate used was changed from 0.5 g to 0.1 g and the reaction time of the chain polymer propagation reaction to propagate the chain polymer using N-hydroxysuccinimide methacrylate was changed from an hour to 15 minutes.

The results of each measurement carried out in the same manner as in Example 1 are shown in Table 1.

Comparative Example 3

The magnetic beads 8 in which a block copolymer of HEAA and MAA binds to the surface (volume average particle diameter: 3.0 μm) were obtained in the same operations as in Example 1, except that the beads (A) were changed to the beads (C) obtained in Synthetic Example 4.

The results of each measurement carried out in the same manner as in Example 1 are shown in Table 1.

Test Example 1

In 2 mL of water, 1 mg of magnetic beads obtained in each Example and Comparative Example were dispersed. This water dispersion was charged into an Eppendorf tube, and the beads were separated using magnetism to remove a supernatant. Next, to the beads, 100 μL of a Jurkat cell disrupted liquid (comprising 100 μg of protein impurities) was added and incubated for 30 minutes. The beads were then separated using magnetism to remove a supernatant, and the beads were washed 5 times with a TBS-T (0.05 mass % Tween 20) buffer.

Further, the beads were separated using magnetism to remove a supernatant, and an aqueous solution of sodium dodecylbenzenesulfonate (0.5 mass %) was then added to detach nonspecifically adsorbing protein impurities from the beads. This detaching solution was subjected to SDS-polyacrylamide gel electrophoresis, and the gel was subjected to CBB stain to visually observe the amount of protein nonspecifically adsorbing to the beads, and evaluation was carried out by the following criteria.

It is evaluated that the beads with a less amount of protein are good beads with less nonspecific adsorption. The evaluation results are shown in Table 2.

(Evaluation Criteria)
A: Protein adsorption is not observed, very good,
B: protein adsorption is hardly observed, good, and
C: protein adsorption is clearly observed, not good.

Test Example 2

In 2 mL of water, 1 mg of magnetic beads obtained in each Example and Comparative Example were dispersed. This water dispersion was charged into an Eppendorf tube, and the beads were separated using magnetism to remove a supernatant. Next, the beads were dispersed in 990 μL of a MES buffer (100 mM, pH 5.0), and 10 μL of 1-ethyl-3-(3-dimethylaminopropyl)carbodiimide hydrochloride (10 mg/mL) was added and the obtained mixture was incubated at room temperature for 30 minutes. The beads were separated using magnetism to remove a supernatant and dispersed in 1 mL of a MES buffer (100 mM, pH 5.0), and 15 μg of anti-TSH antibody (manufactured by Funakoshi Co., Ltd.) was added. After incubation at room temperature for 12 hours, the beads were separated using magnetism to remove a supernatant. The beads were washed 5 times with a TBS-T (0.05 mass % Tween 20) buffer to obtain antibody-binding beads. The amount of bound antibody was measured by BCA Assay.

The results are shown in Table 2.

TABLE 1

|  | a | b | c | CONTENT RATIO (a/b) | CONTENT RATIO (c/b) | POLYMER DENSITY (polymer chains/nm$^2$) | Mn | Mw | Mw/Mn | REACTIVE FUNCTIONAL GROUP AMOUNT (μmol/g) |
|---|---|---|---|---|---|---|---|---|---|---|
| EXAMPLE 1 | 35 | 157 | 122 | 0.22 | 0.78 | 1.0 | 17,000 | 18,700 | 1.1 | 100 |
| EXAMPLE 2 | 23 | 145 | 122 | 0.16 | 0.84 | 1.0 | 16,000 | 19,200 | 1.2 | 66 |
| EXAMPLE 3 | 9 | 124 | 115 | 0.07 | 0.93 | 1.0 | 14,000 | 16,800 | 1.2 | 26 |
| EXAMPLE 4 | 14 | 72 | 58 | 0.19 | 0.81 | 1.0 | 13,300(*1) | 16,000(*1) | 1.2(*1) | 39 |
| EXAMPLE 5 | 33 | 169 | 136 | 0.20 | 0.80 | 0.3 | 18,500 | 22,200 | 1.2 | 28 |
| COMPARATIVE EXAMPLE 1 | 58 | 171 | 113 | 0.34 | 0.66 | 1.0 | 18,000 | 19,800 | 1.1 | 165 |
| COMPARATIVE EXAMPLE 2 | 3 | 140 | 137 | 0.02 | 0.98 | 1.0 | 16,000 | 17,800 | 1.1 | 7 |
| COMPARATIVE EXAMPLE 3 | 35 | 157 | 122 | 0.22 | 0.78 | 0.08 | 17,000 | 20,400 | 1.2 | 6 |

(*1)Data on precursor (block copolymer of CBMA and HEAA)

TABLE 2

|  | EFFECT OF SUPPRESSING NONSPECIFIC ADSORPTION | AMOUNT OF BOUND ANTIBODY (μg/mg beads) |
|---|---|---|
| EXAMPLE 1 | B | 12 |
| EXAMPLE 2 | A | 10 |
| EXAMPLE 3 | A | 7 |
| EXAMPLE 4 | A | 10 |
| EXAMPLE 5 | B | 6 |
| COMPARATIVE EXAMPLE 1 | C | 12 |
| COMPARATIVE EXAMPLE 2 | B | 1 |
| COMPARATIVE EXAMPLE 3 | C | 1 |

As shown in Table 2, the magnetic beads obtained in each Example were those to which a ligand easily binds, and in which nonspecific adsorption is suppressed.

What is claimed is:

1. A ligand-binding solid-phase support, formed by binding a ligand to a solid-phase support,
   wherein the solid-phase support is formed by binding a chain polymer at least to the surface,
   wherein the chain polymer is a block polymer comprising
      a first block constituted from repetitions of a hydrophilic structural unit, which is a zwitterionic structure, and
      a second block constituted from repetitions of a structural unit having a reactive functional group,
   wherein a content ratio of the number of moles "a" of the reactive functional group contained in the chain polymer and the number of moles "b" of the whole structural unit contained in the chain polymer, (a/b), is from 0.03 to 0.25, and
   wherein a density of the chain polymer occupying the surface of the solid-phase support is 0.1 polymers/nm$^2$ or more.

2. The ligand-binding solid-phase support according to claim 1, wherein the ligand is an antibody, an antigen, a nucleic acid, a nucleotide, a nucleoside, a protein, a peptide, an amino acid, a polysaccharide, a saccharide, a lipid, a vitamin, medicine, a substrate, a hormone or a neurotransmitter.

3. The ligand-binding solid-phase support according to claim 1 for immunoassay or detecting nucleic acids.

4. The ligand-binding solid-phase support according to claim 1, wherein the first block is a block directly binding to the surface of the solid-phase support.

5. The ligand-binding solid-phase support according to claim 1, wherein the reactive functional group is a reactive functional group selected from the group consisting of a carboxy group, a tosyl group, an amino group, an epoxy group, an acyl group, and an azide group.

6. The ligand-binding solid-phase support according to claim 1, wherein the density of the chain polymer occupying the surface of the solid-phase support is from 0.1 to 2 polymers/nm$^2$.

7. The ligand-binding solid-phase support according to claim 1, wherein a molecular weight distribution of the chain polymer is from 1.0 to 2.5.

8. The ligand-binding solid-phase support according to claim 1, wherein a number average molecular weight of the chain polymer is from 1,000 to 100,000.

9. The ligand-binding solid-phase support according to claim 1, wherein the solid-phase support is a bead.

10. The ligand-binding solid-phase support according to claim 9, wherein the solid-phase support is a magnetic bead.

11. The ligand-binding solid-phase support according to claim 1, wherein a content of the reactive functional group is from 1 to 300 μmol per g of solid content in the solid-phase support.

12. The ligand-binding solid-phase support according to claim 1, wherein the content ratio a/b is from 0.13 to 0.25.

13. The ligand-binding solid-phase support according to claim 1, wherein the content ratio a/b is from 0.03 to 0.22.

* * * * *